United States Patent
Kalb et al.

(10) Patent No.: US 11,284,988 B2
(45) Date of Patent: Mar. 29, 2022

(54) METHOD FOR PRODUCING BIOCORRODIBLE MAGNESIUM ALLOY IMPLANT

(71) Applicant: Biotronik AG, Buelach (CH)

(72) Inventors: Hermann Kalb, Schnaittach (DE); Alexander Rzany, Nuremberg (DE); Bodo Gerold, Karlstadt (DE)

(73) Assignee: BIOTRONIK AG, Buelach (CH)

( * ) Notice: Subject to any disclaimer, the term of this patent is extended or adjusted under 35 U.S.C. 154(b) by 684 days.

(21) Appl. No.: 16/038,446

(22) Filed: Jul. 18, 2018

(65) Prior Publication Data

US 2018/0318063 A1    Nov. 8, 2018

Related U.S. Application Data

(62) Division of application No. 13/977,323, filed as application No. PCT/EP2012/051669 on Feb. 1, 2012, now Pat. No. 10,052,188.

(60) Provisional application No. 61/446,051, filed on Feb. 24, 2011.

(51) Int. Cl.
| | |
|---|---|
| *A61F 2/06* | (2013.01) |
| *A61L 27/04* | (2006.01) |
| *A61L 27/30* | (2006.01) |
| *A61L 27/58* | (2006.01) |
| *A61L 31/02* | (2006.01) |
| *A61L 31/08* | (2006.01) |
| *A61L 31/14* | (2006.01) |

(52) U.S. Cl.
CPC .............. *A61F 2/06* (2013.01); *A61L 27/047* (2013.01); *A61L 27/306* (2013.01); *A61L 27/58* (2013.01); *A61L 31/022* (2013.01); *A61L 31/088* (2013.01); *A61L 31/148* (2013.01)

(58) Field of Classification Search
CPC ........ A61F 2/06; A61L 27/047; A61L 27/306; A61L 27/58; A61L 31/088; A61L 31/148
USPC .......................................... 148/516
See application file for complete search history.

(56) References Cited

U.S. PATENT DOCUMENTS

| | | |
|---|---|---|
| 2007/0191708 A1 | 8/2007 | Gerold et al. |
| 2007/0227629 A1 | 10/2007 | Gerold et al. |
| 2008/0033576 A1 | 2/2008 | Gerold et al. |
| 2010/0256747 A1 | 10/2010 | Hausbeck et al. |
| 2011/0000070 A1 | 1/2011 | Wu |

FOREIGN PATENT DOCUMENTS

| | | |
|---|---|---|
| DE | 102006038238 | 2/2008 |
| EP | 2236163 | 10/2010 |

OTHER PUBLICATIONS

Lopez-Garcia, International Search Report for International Application No. PCT/EP2012/051669, dated Mar. 30, 2012.

*Primary Examiner* — Jie Yang
(74) *Attorney, Agent, or Firm* — Greer, Burns & Crain, Ltd.; Steven P. Fallon

(57) ABSTRACT

A method forms an implant with a base body made of a biocorrodible magnesium alloy. The methods make magnesium alloy that contains a plurality of statistically distributed particles, with one or more of the elements Y, Zr, Mn, Sc, Fe, Ni, Co, W, Pt and noble earths with the atomic numbers 57 to 71, or the particles comprise alloys or compounds containing one or more of the elements mentioned. The mean distance of the particles from each other is smaller than the hundredfold mean particle diameter.

4 Claims, No Drawings

METHOD FOR PRODUCING BIOCORRODIBLE MAGNESIUM ALLOY IMPLANT

CROSS REFERENCE

The present application claims priority from and is a 35 U.S.C. §§ 120 and 121 divisional of U.S. application Ser. No. 13/977,323, which was a 35 U.S.C. § 371 National Stage application which claims priority to International Application No. PCT/EP2012/051669 filed on Feb. 1, 2012, which application claims priority to U.S. provisional patent application Ser. No. 61/446,051 filed on Feb. 24, 2011 under 35 U.S.C. § 119(e); all of which applications are incorporated herein by reference.

TECHNICAL FIELD

One aspect of the invention relates to an implant comprising a base body made of a biocorrodible magnesium alloy.

BACKGROUND

Implants are being employed in a wide variety of forms in modern medical technology. They are used, for example, to support vessels, hollow organs and vein systems (endovascular implants, such as stents), for fastening and the temporary fixation of tissue implants and tissue transplantations, but also for orthopedic purposes, such as nails, plates or screws. A particularly frequently used form of an implant is the stent. Implant materials comprise polymers, metallic materials, and ceramic materials (as coatings, for example). Biocompatible metals and metal alloys for permanent implants comprise, for example, stainless steels (such as 316L), cobalt-based alloys (such as CoCrMo cast alloys, CoCrMo forge alloys, CoCrWNi forge alloys and CoCrNiMo forge alloys), technical pure titanium and titanium alloys (such as cp titanium, TiAl6V4 or TiAl6Nb7) and gold alloys. In the field of biocorrodible stents, the use of magnesium or technical pure iron as well as biocorrodible base alloys of the elements magnesium, iron, zinc, molybdenum, and tungsten are proposed. Aspects of the present invention relate to biocorrodible magnesium base alloys.

The implantation of stents has become established as one of the most effective therapeutic measures for the treatment of vascular diseases. Stents have the purpose of performing a stabilizing function in hollow organs of a patient. For this purpose, stents featuring conventional designs have a filigree supporting structure comprising metal braces, which is initially present in compressed form for introduction into the body and is expanded at the site of the application. One of the main application areas of such stents is to permanently or temporarily dilate and hold open vascular constrictions, particularly constrictions (stenoses) of the coronary blood vessels. In addition, aneurysm stents are also known, which are used primarily to seal the aneurysm. The support function is additionally provided.

Stents comprise a peripheral wall with sufficient load-bearing capacity to hold the constricted vessel open to the desired extent and a tubular base body through which the blood continues to flow without impairment. The peripheral wall is generally formed by a lattice-like supporting structure, which allows the stent to be introduced in a compressed state, in which it has a small outside diameter, all the way to the stenosis of the particular vessel to be treated and to be expanded there, for example by way of a balloon catheter, so that the vessel has the desired, enlarged inside diameter. As an alternative, shape memory materials such as nitinol have the ability to self-expand when a restoring force is eliminated that keeps the implant at a small diameter. The restoring force is generally applied to the material by a protective tube.

The implant, notably the stent, has a base body made of an implant material. An implant material is a non-living material, which is used for applications in medicine and interacts with biological systems. A basic prerequisite for the use of a material as implant material, which is in contact with the body environment when used as intended, is the body friendliness thereof (biocompatibility). Biocompatibility shall be understood as the ability of a material to evoke an appropriate tissue response in a specific application. This includes an adaptation of the chemical, physical, biological, and morphological surface properties of an implant to the recipient's tissue with the aim of a clinically desired interaction. The biocompatibility of the implant material is also dependent on the temporal course of the response of the biosystem in which it is implanted. For example, irritations and inflammations occur in a relatively short time, which can lead to tissue changes. Depending on the properties of the implant material, biological systems thus react in different ways. According to the response of the biosystem, the implant materials can be divided into bioactive, bioinert and degradable or resorbable materials.

Implant materials comprise polymers, metallic materials, and ceramic materials (as coatings, for example). Biocompatible metals and metal alloys for permanent implants comprise, for example, stainless steels (such as 316L), cobalt-based alloys (such as CoCrMo cast alloys, CoCrMo forge alloys, CoCrWNi forge alloys and CoCrNiMo forge alloys), technical pure titanium and titanium alloys (such as cp titanium, TiAl6V4 or TiAl6Nb7) and gold alloys. In the field of biocorrodible stents, the use of magnesium or technical pure iron as well as biocorrodible base alloys of the elements magnesium, iron, zinc, molybdenum, and tungsten are proposed. Aspects of the present invention relate to biocorrodible magnesium base alloys.

The use of biocorrodible magnesium alloys for temporary implants having filigree structures is made difficult in particular in that the degradation of the implant progresses very quickly in vivo. So as to reduce the corrosion rate, this being the degradation speed, different approaches are being discussed. For one, it is attempted to slow the degradation on the part of the implant material by developing appropriate alloys. In addition, coatings are to bring about a temporary inhibition of the degradation. While the existing approaches are promising, none of them has so far been implemented in a commercially available product. Regardless of the efforts made so far, there is rather a continuing need for solutions that make it possible to at least temporarily reduce the in vivo corrosion of magnesium alloys.

SUMMARY

One or more of the disadvantages of the prior art mentioned above are solved, or at least mitigated, by the implant according to the invention. One embodiment of the implant according to the invention comprises a base body made of a biocorrodible magnesium alloy. The magnesium alloy contains a plurality of statistically distributed particles, comprising one or more of the elements Y, Zr, Mn, Sc, Fe, Ni, Co, W, Pt and noble earths with the atomic numbers 57 to 71, or alloys, or compounds containing one or more of these elements. The mean distance of the particles from each other is smaller than the hundredfold mean particle diameter. Put another way, the statistical mean distance between the particles is less than 100× (average particle diameter). In some embodiments, the statistical mean distance between particles is less than 50× (average particle diameter).

A method for producing an implant having a base body of a biocorrodible magnesium alloy includes providing a blank made of the biocorrodible magnesium alloy. A non-aqueous suspension of particles to is applied to the blank. The particles include one or more of the elements Y, Zr, Mn, Sc, Fe, Ni, Co, W, Pt, and noble earths with the atomic numbers from 57 to 71, or alloys, or compounds containing one or more of these elements. The particles are rolled into the surface or into the near-surface region of the blank to thereby result in the magnesium alloy containing a plurality of statistically distributed particles, wherein the mean distance of the particles from each other is smaller than the hundredfold mean particle diameter, and the particles are incorporated into a surface or into a near-surface region of the base body.

A method for producing an implant having a base body of a biocorrodible magnesium alloy, includes providing a blank made of the biocorrodible magnesium alloy. Particles are applied to the blank. The particles include one or more of the elements Y, Zr, Mn, Sc, Fe, Ni, Co, W, Pt, and noble earths with the atomic numbers from 57 to 71, or alloys, or compounds containing one or more of these elements. The magnesium alloy is melted in the near-surface region of the blank to result in the magnesium alloy containing a plurality of statistically distributed particles, wherein the mean distance of the particles from each other is smaller than the hundredfold mean particle diameter, and the particles are incorporated into a surface or into a near-surface region of the base body.

In the development of magnesium materials so far, the corrosion resistance has always been improved by increasing the purity of the magnesium material. Iron, nickel, chromium, and cobalt are considered to be critical elements in this context. Particles comprising intermetallic compounds, particles of a different chemical nature (oxides, hydrides) or segregations (Al12Mg17) in magnesium materials result in microgalvanic corrosion due to the different electrochemical potential. This results in local corrosive processes, which massively accelerate the corrosion rate of the material. For this reason, previously attempts have been made to minimize the concentration of the particles to the extent possible.

The solution according to the invention, however, exploits the surprising discovery that an effective solution can be achieved by taking exactly the opposite approach of the prior art. In magnesium materials, in general, the corrosion that is observed attacks the material locally very inhomogeneously. In the process, it has been discovered that cathodic processes occur, which are accompanied by the release of hydroxide ions and the development of hydrogen, more specifically at defined centers, namely the above-mentioned particles. The anodic dissolution process of the magnesium material takes place in the surroundings of the cathodic center. The process can be divided into the following partial reactions:

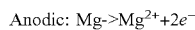
Anodic: $Mg \rightarrow Mg^{2+}+2e^-$

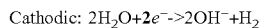
Cathodic: $2H_2O+2e^- \rightarrow 2OH^-+H_2$

It has been discovered that the anodic process is highly dependent on the pH value. For example, the Mg corrosion is massively accelerated at pH<5, while it is massively decelerated at pH>10 and basically completely disrupted. Given this behavior, the release of hydroxide ions on the cathodic center leads to the protection of the direct surroundings.

The invention is based on the discovery that the corrosion of implants made of biocorrodible magnesium alloys can be delayed by adding a plurality of homogenously distributed particles to the material volume, a near-surface region, or the surface. It has been discovered that the particles act as cathodic centers within the above-mentioned meaning, which is to say, the hydrogen overvoltage is sufficiently low and the reaction can take place at a high rate. The particles comprise one or more of the elements Y, Zr, Mn, Sc, Fe, Ni, Co, W, Pt and nobles earths with the atomic numbers 57 to 71, or alloys, or compounds containing one or more of these elements. In the present invention, the term 'alloy' shall cover metallic compositions of the elements, and also compositions in which covalent bonds exist between the elements. The alloys preferably contain magnesium. Compounds comprise in particular hydrides and carbides of the above-mentioned elements.

Preferably, the particles consist of one or more of the elements Y, Zr, Mn, Sc, Fe, Ni, Co, W, Pt and nobles earths with the atomic numbers 57 to 71, or alloys, or compounds consisting of one or more of these elements.

DETAILED DESCRIPTION

With the above summary now presented, detailed description of invention embodiments can now be presented. It will be appreciated that the present invention may be embodied in an implant or in a method for making an implant. Accordingly, it will further be appreciated that when describing an implant embodiment, description of a method for making that implant may also be made, and vice versa. Before discussing particular embodiments, some general definitions are offered for clarity.

Biocorrodible as defined by the invention denotes alloys in the physiological environment of which degradation or remodeling takes place, so that the part of the implant made of the material is no longer present in its entirety, or at least predominantly.

A magnesium alloy in the present case shall be understood as a metal structure, the main constituent of which is magnesium. The main constituent is the alloying constituent having the highest weight proportion in the alloy. The proportion of the main constituent is preferably more than 50% by weight, particularly more than 70% by weight. The alloy is to be selected in the composition thereof such that it is biocorrodible. A possible test medium for testing the corrosion behavior of a potential alloy is synthetic plasma, as that which is required according to EN ISO 10993-15: 2000 for biocorrosion analyses (composition NaCl 6.8 g/l, $CaCl_2$ 0.2 g/l, KCl 0.4 g/l, $MgSO_4$ 0.1 g/l, $NaHCO_3$ 2.2 g/l, $Na_2HPO_4$ 0.126 g/l, $NaH_2PO_4$ 0.026 g/l). For this purpose, a sample of the alloy to be analyzed is stored in a closed sample container with a defined quantity of the test medium at 37° C. and pH 7.38. The samples are removed at intervals—which are adapted to the anticipated corrosion behavior—ranging from a few hours to several months and analyzed for traces of corrosion in the known manner. The synthetic plasma according to EN ISO 10993-15:2000 corresponds to a blood-like medium and thus is a possible medium to reproducibly simulate a physiological environment as defined by the invention.

The term corrosion refers in the present example to the reaction of a metallic material with the environment thereof, wherein a measurable change of the material is caused, which—when using the material in a component—results in an impairment of the function of the component. The corrosion process can be quantified by the provision of a corrosion rate. Swift degradation is associated with a high corrosion rate, and vice versa. Relative to the degradation of the entire base body, an implant that is modified as defined by the invention will result in a decrease of the corrosion rate as compared to the same implant if not modified by the invention.

The particles preferably have a mean diameter of 1 nanometer to 10 micrometers, particularly preferred 500 nanometers to 3 micrometers, and more particularly 1 to 2 micrometers. Other diameters may also prove useful, including those smaller than 1 nanometer and those larger than 10 micrometers.

In the surroundings of the cathodic center, protected regions develop as a result of the release of hydroxide ions. The majority of the protected region around an individual cathodic center depends on the size and composition of the particles and the surrounding matrix of the magnesium material. The size of the protected area per particle should be at least 1 square micrometer, preferably up to 100 square micrometers, with up to 10000 square micrometers being particularly preferred.

Within the material, the area of the protected regions has a size distribution that is determined by the distribution of the particles. The protective effect on the total surface of the magnesium material is dependent on the number and size distribution of the protected regions. The number of particles on the surface of the base body is preferably $1 \times 10^2$ to $1 \times 10^6$ particles per mm$^2$, or the number of particles in the volume of the base body is $1 \times 10^3$ to $1 \times 10^9$ particles per mm$^3$. A ratio of the mean particle diameter to the mean distance of the particles from each other preferably ranges between 1:2 and 1:100, and more particularly between 1:2 and 1:10. Other ratios may be employed.

The corrosion rate is quantitatively influenced by the cathodic centers as follows:

a) The protected total area A_protect is obtained by assuming non-overlapping protected regions from the sum over the distribution of the areas A_cathodic_center protected by the individual cathodic centers:

$$A_{protect} = \sum_{i=1 \ldots N} A_i^{cathodic\ center}$$

where N is the number of particles.

b) The corrosion rate R_corr is directly proportional to the corrosion of the accessible sample area A_corr, wherein A_total denotes the total area of the material:

$$R_{corr} \propto A_{corr} \propto A_{total} - A_{protect} \propto A_{total}\left(1 - \frac{A_{protect}}{A_{total}}\right)$$

As a result, assuming the same abrasion depth, the corrosion rate decreases as the percentage of area of the protected region decreases. The percentages of area mentioned can be determined experimentally.

A particularly high protective effect is achieved precisely when a sufficiently large number of cathodic centers is uniformly distributed in the material, and the overlap between the protected regions is as small as possible. This requires determining an optimal balance between too many and too few particles. It has been discovered that the optimal mean distance d_mean between cathodic centers without overlap can be estimated from a statistical analysis of the distribution:

$$d_{mean} = 2 \cdot \sqrt{\frac{A_{protect}}{N \cdot \pi}}$$

The protective effect can be increased both by a large number of small protected regions and by a small number of large protected regions. In many embodiments, the mean distance between the particles preferably ranges between 200 nm and 100 μm. The mean distance in some embodiments is in particular smaller than 20 μm.

The protected area per cathodic center is dependent on the chemical nature of the cathodic center and the material matrix.

The claimed modification of the material can be applied not only to the entire material volume, but optionally can also be limited to the surface or the near-surface region of an implant. In this way, it is possible to deliberately introduce cathodic centers into the surface of a workpiece by means of rolling. Those knowledgeable in the art understand the meaning of rolling, and the general process this refers to. A detailed discussion of rolling is not necessary for this reason and will be avoided for the additional sake of brevity. In general, rolling is a process in which heated metal stock is shaped as desired by passing between two opposing wheels that "roll" the stock into a piece of a desired thickness. Hot rolling generally refers to rolling performed at temperatures above the metal's recrystalization temperature, and cold rolling to rolling performed at temperatures below the recrystalization temperature. It has been discovered that rolling within the scope of the invention as described above creates an initial corrosion barrier, and the degradation rate increases over time. The particles are preferably incorporated in the surface or the near-surface region of the base body. A relatively low corrosion rate then occurs at the beginning of the onsetting corrosive processes, said rate increasing over the course of time. This behavior is referred to as temporarily reducing the corrosion rate. In the case of coronary stents, the mechanical integrity of the structure should be maintained for a period of three to six months after implantation.

Implants as defined by the invention are devices introduced into the body by a surgical procedure and comprise fastening elements for bones, such as screws, plates or nails, surgical suture material, intestinal clamps, vessel clips, prostheses in the area of hard and soft tissues, and anchoring elements for electrodes, particularly for pacemakers or defibrillators. The implant is made entirely or partially of the biocorrodible material. If only a part of the implant is made of the biocorrodible material, this part is to be modified accordingly. The implant is preferably a stent.

A further concept of the invention is to provide two methods for producing an implant comprising a main body made of a biocorrodible magnesium alloy, wherein the magnesium alloy contains a plurality of statistically distributed particles having the above-mentioned composition, and the mean distance of the particles from each other is smaller than the hundredfold mean particle diameter, and the particles are incorporated in the surface or in a near-surface region of the base body.

According to a first embodiment, a method of the invention comprises the following steps:
(i) providing a blank made of the biocorrodible magnesium alloy;
(ii) applying a non-aqueous suspension of particles having the above-mentioned composition to the blank; and
(iii) rolling the particles into the surface or into the near-surface region of the blank.

Accordingly, an oily suspension containing the particles to incorporated is applied to the blank, from which the base body is to be shaped, and incorporated by rolling. This suspension can be used as a lubricant both during cold rolling and during hot rolling. By optimizing the volume flow of the suspension, temperature, contact pressure and speed, the incorporation of the particles in the surface of the rolled magnesium material can be optimized. The variant is suited in particular for magnesium alloys based on WE43.

According to a second embodiment, a method comprises the following steps:
(i) providing a blank made of the biocorrodible magnesium alloy;
(ii) applying particles having the above-mentioned composition to the blank; and
(iii) melting the magnesium alloy onto the near-surface region of the blank.

According to this variant, the particles to be incorporated are applied directly onto the blank, which later forms the base body. After that, the magnesium alloy is locally melted on the surface, for example by laser treatment. After cooling, the particles are then embedded in the near-surface region of the blank.

According to the two methods for producing an implant, the particles preferably consist of preferably, the particles consist of one or more of the elements Y, Zr, Mn, Sc, Fe, Ni, Co, W, Pt and nobles earths with the atomic numbers 57 to 71, or alloys, or compounds consisting of one or more of these elements.

The invention will be explained in more detail hereinafter based on some example embodiments.

EMBODIMENT 1

An iron particle-containing (chemicals for the production are available from Sigma-Aldrich, particle diameter smaller than 100 nm) suspension is applied, for example by spraying or immersion, onto a plate-shaped blank made of the magnesium alloy AZ31 so as to generate a film having a statistically homogeneous distribution of iron particles. The carrier fluid for the suspension may be selected form any of a number of suitable alternatives.

This suspension can be used as a lubricant both during cold rolling and during hot rolling. The particles are incorporated in the surface of the blank by the rolling process. The particles not only increase the corrosion protection, but also the wear resistance by increasing the hardness. The blank is subsequently processed into the base body of the implant.

EMBODIMENT 2

Tungsten particles (available from Sigma-Aldrich; particle diameter approximately 150 nm, other useful diameters ranges including, for example, 100 nm-200 nm) are applied in the form of a powder onto a plate-shaped blank made of the magnesium alloy AZ31 and homogeneously distributed by shaking. When using complicated three-dimensional structures, it is also advantageous to use an adhesion-promoting polymer to coat the surface before the laser alloying process. Many suitable polymers will be apparent to those knowledgeable in the art. By varying the polymer to tungsten particle ratio, it is possible to directly adjust the mean distance between tungsten particles.

The tungsten particles are incorporated into the magnesium alloy by laser alloying. To this end, the workpiece is locally melted using a high-performance laser diode under argon inert gas. The laser output is between 1.2 and 1.6 kW, and the feed rate of the laser is 0.5 to 1.0 m/min. The use of the argon prevents an oxidation of the magnesium material and of the tungsten during processing.

Using the laser alloying technology, it is possible in particular to locally protect a workpiece made of a magnesium alloy. In connection with stents, for example, sequential fragment of the implant can be achieved by locally influencing the degradation rate, for example by providing the surfaces of the segment rings of a stent structure, but not the longitudinal connecting struts of the segment rings, with cathodic centers according to the invention, whereby the struts degrade more quickly than the segment rings. Because the connecting struts dissolve more quickly, high longitudinal flexibility is achieved quickly, wherein the load-bearing capacity of the segment rings is still maintained.

The particles provide not only corrosion protection, but also increase the wear resistance against abrasion by increasing the hardness. In addition, by suitably selecting the particles and the composition thereof, polymeric substances can be effectively bonded to the surface. These polymeric substances can have a corrosion-inhibiting effect on the one hand, and on the other hand, they may contain one or more pharmacological active ingredients, or exhibit a pharmacological effect themselves.

The additional coating with a polymer can be technically implemented, for example, as follows. PLLA L214S (Boehringer Ingelheim) is dissolved in a concentration of 1.6% (w/v) in chloroform and rapamycin is added as the active substance. The active ingredient content preferably ranges between 15% and 20%, in relation to the solid matter content. The implant made of the modified magnesium alloy is immersed for 1 second into the solution using an underwater robot, pulled out, and air containing nitrogen is blown on so as to evaporate the solvent. This process is repeated until a sufficient layer thickness of approximately 5 μm has been reached.

The embodiments also apply analogously to other biocorrodible magnesium alloys and particle compositions.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope is of this invention.

What is claimed is:

1. A method for producing an implant having a base body comprising a biocorrodible magnesium alloy, wherein the method comprises the following steps:
(i) providing a blank made of the biocorrodible magnesium alloy;
(ii) applying a non-aqueous suspension of particles to the blank, the particles comprising one or more of the elements Y, Zr, Mn, Sc, Fe, Ni, Co, W, Pt, and noble earths with the atomic numbers from 57 to 71, or alloys, or compounds containing one or more of these elements; and (iii) rolling the particles into the blank to incorporate a plurality of statistically distributed particles into the magnesium alloy, wherein the mean distance of the particles from each other in the magnesium alloy is smaller than the hundredfold mean particle diameter.

2. A method according to claim 1, wherein the particles consist of one or more of the elements Y, Zr, Mn, Sc, Fe, Ni, Co, W, Pt, and noble earths with the numbers 57 to 71, or alloys, or compounds consisting of one or more of these elements.

3. A method according to claim 1, and further including the step of providing the particles in a quantity to result in the number of the particles in the volume of the base body to range between $1\times10^3$ and $1\times10^9$ per mm$^3$, and wherein the particles have a mean diameter of 1 nm to 10 µm.

4. A method according to claim 1, and further comprising the step of providing the particles in a quantity and are distributed to result in a mean distance between the particles being between 200 nm and 100 µm.

\* \* \* \* \*